United States Patent [19]

Junino et al.

[11] Patent Number: 5,667,792
[45] Date of Patent: *Sep. 16, 1997

[54] DERIVATIVES OF 2,5-DIHYDROXYPHENYLCARBOXYLIC ACIDS, AND THEIR UTILIZATION IN COSMETIC OR DERMATOLOGICAL COMPOSITIONS WITH A DEPIGMENTING ACTION

[75] Inventors: Alex Junino, Livry Gargan; Alain Lagrange, Chatoh; Quang Lan N'Guyen, Antony; Marie-Alix Bourboulon, Paris, all of France

[73] Assignee: L'Oreal, Paris, France

[*] Notice: The term of this patent shall not extend beyond the expiration date of Pat. No. 5,587,173.

[21] Appl. No.: 684,705

[22] Filed: Jul. 19, 1996

Related U.S. Application Data

[62] Division of Ser. No. 465,105, Jun. 5, 1995, Pat. No. 5,587,173, which is a division of Ser. No. 913,950, Jul. 17, 1972, Pat. No. 5,449,518.

[30] Foreign Application Priority Data

Jul. 17, 1991 [FR] France .................. 91 09029

[51] Int. Cl.$^6$ ...................... A61K 7/42
[52] U.S. Cl. ............ 424/401; 424/62; 424/450; 424/489; 564/170; 514/237.5; 514/257; 514/317; 514/423; 514/622; 514/846; 514/937; 514/938; 514/943; 514/944
[58] Field of Search ............ 424/401, 62, 450, 424/489; 564/170; 514/237.5, 255, 317, 423, 622, 846, 937, 938, 943, 944

[56] References Cited

U.S. PATENT DOCUMENTS

| | | | |
|---|---|---|---|
| 4,185,958 | 1/1980 | Bugaut et al. | 8/101 |
| 4,289,495 | 9/1981 | Bugaut et al. | 8/406 |
| 4,484,000 | 11/1984 | Howell | 560/75 |
| 4,526,779 | 7/1985 | Hashimoto | 424/62 |
| 4,545,984 | 10/1985 | Moller et al. | 424/70 |
| 4,835,323 | 5/1989 | Howell | 568/562 |
| 5,587,173 | 12/1996 | Junino et al. | 424/401 |

FOREIGN PATENT DOCUMENTS

| | | |
|---|---|---|
| 0069068 | 1/1983 | European Pat. Off. . |
| 2400359 | 3/1979 | France . |
| 2401900 | 3/1979 | France . |
| 2400358 | 7/1981 | France . |
| 61-27909 | 2/1986 | Japan . |
| 82/04189 | 12/1982 | WIPO . |

*Primary Examiner*—Jyothsan Venkat
*Attorney, Agent, or Firm*—Oliff & Berridge

[57] ABSTRACT

A cosmetic or dermatological composition with a depigmenting action comprises derivatives of 2,5-dihydroxyphenylcarboxylic acids, their homologs, and their salts, with the derivatives having the following structural formula:

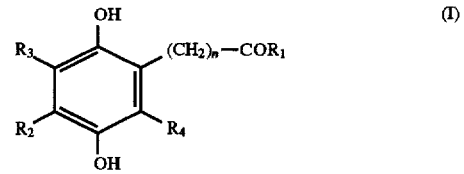

wherein:
$R_1$ represents $OR_5$, OH, or

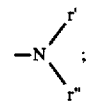

$R_5$ is a linear or branched $C_1$-$C_{20}$ alkyl radical, a linear or branched $C_2$-$C_{20}$ alkenyl radical, or a $C_1$-$C_{20}$ alkyl radical substituted by one or more hydroxy or alkoxy groups;
r' and r", identical or different, represent a hydrogen atom, a $C_1$-$C_{20}$ alkyl radical, a $C_2$-$C_6$ hydroxyalkyl radical, or a $C_3$-$C_6$ polyhydroxyalkyl, or r' and r" taken together, with the nitrogen atom, form a heterocycle;
the number of carbon atoms in the —$(CH_2)_n$—$COR_1$ chain is less than or equal to 21;
$R_2$ and $R_3$, identical or different, represent a hydrogen atom, a linear or branched $C_1$-$C_4$ alkyl radical, or a $C_1$-$C_4$ alkoxy; $R_4$ represents a hydrogen atom or a linear or branched C-$C_4$ alkyl radical; and
n is an integer from 0 to 20, provided that, when $R_2$ and $R_3$ represent a hydrogen atom, n is greater than or equal to 2.

10 Claims, No Drawings

DERIVATIVES OF 2,5-DIHYDROXYPHENYLCARBOXYLIC ACIDS, AND THEIR UTILIZATION IN COSMETIC OR DERMATOLOGICAL COMPOSITIONS WITH A DEPIGMENTING ACTION

This is a Division of application Ser. No. 08/465,105 filed Jun. 5, 1995 now U.S. Pat. No. 5,587,173, which is a Division of application Ser. No. 07/913,950, filed Jul. 17, 1992 now U.S. Pat. No. 5,449,518.

The present invention relates to the use of derivatives of 2,5-dihydroxyphenylcarboxylic acids, their homologs, and their salts for the preparation of cosmetic or dermatological compositions which when topically applied, bleach the skin or treat pigmented spots. The invention also relates to novel homologs of 2,5-dihydroxyphenylcarboxylic acid.

BACKGROUND

The mechanism by which skin pigmentation is formed, namely by which melanins are formed, is particularly complex and schematically involves the following main steps: Tyrosine→Dopa→Dopaquinone→Dopachrome→Melanins, with the enzyme involved in this series of reactions being essentially tyrosinase.

The substances in widest use at the present time as depigmentors are in particular hydroquinone and its derivatives, particularly its ethers such as hydroquinone monomethyl ether.

These compounds, while they are definitely effective, are unfortunately not bereft of side effects, which can make their use delicate or even dangerous.

Thus, hydroquinone, whose use is moreover limited to a concentration of 2%, is a compound that is particularly irritating and cytotoxic to the melanocyte, and whose total or partial replacement has been considered by many authors.

Thus, U.S. Pat. No. 4,526,779 has proposed certain hydroquinone fatty esters that have good activity and are less irritating and more stable than hydroquinone.

Likewise, other hydroquinone derivatives that do not have the drawbacks of hydroquinone but whose efficacy has proved relatively poor have been proposed in Japanese Patent Application No. 27909/86.

It is well established that a substance has a depigmenting effect if it acts directly on the vitality of the epidermal melanocytes where melanogenesis normally occurs and/or if it interferes with one of the stages in melanin biosynthesis, either by inhibiting one of the enzymes involved or by intercalation as a structural analog in the synthesis pathway which can accordingly be blocked, hence the depigmenting effect.

The use of topical depigmentors that have good efficacy and are harmless is particularly desirable with a view to treating regional hyperpigmentation caused by melanocytic hyperactivity such as idiopathic melasma occurring during pregnancy (mask of pregnancy or chloasma) or secondary to estrogen-progesterone contraception; local hyperpigmentation caused by benign melanocytic hyperactivity and proliferation such as lentigo senilis, or liver spots; accidental hyperpigmentation such as postlesional photosensitization and scarring; and certain forms of leukoderma such as vitiligo where, if the injured skin cannot be repigmented, the residual zones of normal skin are depigmented to impart a homogeneous white color to the entire skin.

SUMMARY OF THE INVENTION

After numerous studies on a number of substances, it has surprisingly been found that certain 2,5-dihydroxyphenylcarboxylic acid derivatives, their homologs, and their salts have particularly pronounced depigmenting action which is distinctly superior to that of hydroquinone in an in vitro tyrosinase activity inhibition test.

Hence, an object of the present invention is the use of derivatives of 2,5-dihydroxyphenylcarboxylic acids, their homologs, and their salts for preparing a cosmetic or dermatological composition with a depigmenting action, said derivatives having the following structural formula:

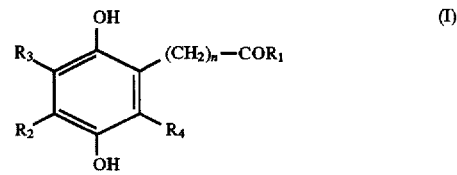

wherein:

$R_1$ represents $OR_5$, OH, or

$R_5$ is a linear or branched $C_1$-$C_{20}$ alkyl radical, a linear or branched $C_2$-$C_{20}$ alkenyl radical, or a $C_1$-$C_{20}$ alkyl radical substituted by one or more hydroxy or alkoxy groups;

r' and r", identical or different, represent a hydrogen atom, a $C_1$-$C_{20}$ alkyl radical, a $C_2$-$C_6$ hydroxyalkyl radical, or a $C_3$-$C_6$ polyhydroxyalkyl radical, or r' and r" taken together, with the nitrogen atom, form a heterocycle;

the number of carbon atoms in the —$(CH_2)_n$—$COR_1$ chain is less than or equal to 21;

$R_2$ and $R_3$, identical or different, represent a hydrogen atom, a linear or branched $C_1$-$C_4$ alkyl radical, or a $C_1$-$C_4$ alkoxy;

$R_4$ represents a hydrogen atom or a linear or branched $C_1$-$C_4$ alkyl radical; and n is an integer from 0 to 20, provided that, when $R_2$ and $R_3$ represent a hydrogen atom, n is greater than or equal to 2.

DETAILED DESCRIPTION OF PREFERRED EMBODIMENTS

According to a preferred embodiment of the invention, examples of a suitable $C_1$-$C_{20}$ alkyl radical include a methyl, ethyl, propyl, isopropyl, butyl, tertiary butyl, isoamyl, octyl, 2-ethylhexyl, dodecyl, tetradecyl, hexadecyl, or octadecyl radical.

An example of a suitable $C_2$-$C_{20}$ alkenyl radical is the oleyl radical.

An example of a suitable $C_1$-$C_{10}$ alkyl radical substituted by one or more hydroxy or alkoxy groups is a hydroxymethyl, 2-hydroxyethyl, 2-hydroxypropyl, 3-hydroxypropyl, 4-hydroxybutyl, 5-hydroxypentyl, 6-hydroxyhexyl, methoxyethyl, or ethoxymethyl radical.

An example of a suitable $C_2$-$C_6$ hydroxyalkyl radical is a 2-hydroxyethyl, 2-hydroxypropyl, or 3-hydroxypropyl radical.

An example of a suitable $C_3$-$C_6$ polyhydroxyalkyl radical is a radical having 3 to 6 carbon atoms and 2 to 5 hydroxyl groups such as the 2,3-dihydroxypropyl, 2,3,4-trihydroxybutyl, or 2,3,4,5-tetrahydroxypentyl radical.

An example of a suitable $C_1$-$C_4$ alkoxy radical is a methoxy, ethoxy, propoxy, isopropoxy, or butoxy radical.

When r' and r" taken together form a heterocycle with the nitrogen atom, this can be a morpholino, pyrrolidino, piperidino, piperazino ring, or piperazino ring substituted by $C_1$-$C_4$ alkyl or $C_2$-$C_6$ hydroxyalkyl.

The 2,5-dihydroxyphenylcarboxylic acid derivatives with structural formula (I) are known for the most part and have been described in French Patents Nos. 7824174 (2,400,358) and 7824175 (2,400,359).

Examples of compounds with general formula (I) include the following:

2,5-dihydroxyphenylpropionic acid and its ethyl and lauric esters, 2,5-dihydroxy-3,4-dimethylphenylacetic acid and its ethyl ester, methyl 2,5-dihydroxy-4-methylphenylacetate, 2,5-dihydroxy-4-methylphenylacetic acid, 2,5-dihydroxy-4-methylphenylpropionic acid and its ethyl ester, 2,5-dihydroxy-4-methylbenzoic acid and its methyl or ethyl ester, 2,5-dihydroxy-4-ethylbenzoic acid, 2,5-dihydroxy-4-methoxybenzoic acid and its methyl ester, 2,5-dihydroxy-4-ethoxybenzoic acid, 3-(2,5-dihydroxy-4'-methylphenyl)-1-N(ω-carboxydecyl)propylamide, 2,5-dihydroxy-4-methylphenylbutanoic acid, 2,5-dihydroxy-4-methylphenylhexanoic acid, 2,5-dihydroxy-4-methoxyphenylacetic acid and its methyl ester, 2,5-dihydroxy-4-methoxyphenylacetamide, methyl ester of 2,5-dihydroxy-3-methoxyphenylacetic acid, 2,5-dihydroxy-3-methoxyphenylpentadecanoic acid and its methyl ester, 2,5-dihydroxyphenylbutanoic acid and its methyl ester, 2,5-dihydroxyphenylbutylamide, 2,5-dihydroxyphenylpentanoic acid, 2,5-dihydroxyphenylpentylamide, 2,5-dihydroxyphenylhexanoic acid, 2,5-dihydroxyphenyloctanoic acid, 2,5-dihydroxyphenyldecanoic acid and its ethyl ester, 2,5-dihydroxyphenylundecanoic acid and its methyl ester, 2,5-dihydroxy-3,4-dimethylphenylbutanoic acid, 2,5-dihydroxy-3,4-dimethoxyphenylacetic acid, ethyl ester of 2,5-dihydroxy-4,6-dimethylphenylacetic acid, 2-(2,5-dihydroxy-4-methylphenyl)-N-octylacetamide, and 6-(2,5-dihydroxy-4-methoxyphenyl)hexanoic acid.

According to a preferred embodiment of the invention, the derivatives of 2,5-dihydroxyphenylcarboxylic acids, their homologs, and their salts have the following general formula (II):

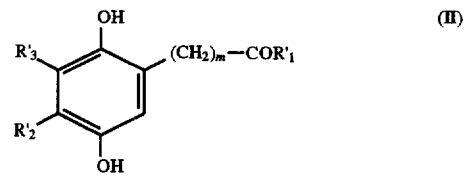

wherein:

$R'_1$ has the same meaning as given hereinabove for $R_1$ according to formula (I);

m is 1 or 2;

(i) when m is 1, at least one of the radicals $R'_2$ and $R'_3$ represents a linear or branched $C_1$-$C_4$ alkyl radical, and the other can represent a hydrogen atom, and (ii) when m is 2, $R'_2$ and $R'_3$, which are identical or different, represent a hydrogen atom or a linear or branched $C_1$-$C_4$ alkyl radical.

Examples of compounds with general formula (II) include the following:

2,5-dihydroxyphenylpropionic acid, 2,5-dihydroxy-3,4-dimethylphenylacetic acid, methyl 2,5-dihydroxy-4-methylphenylacetate, 2,5-dihydroxy-4-methylphenylacetic acid, and 2,5-dihydroxy-4-methylphenylpropionic acid.

In the depigmenting compositions according to the present invention, the concentration of 2,5-dihydroxyphenylcarboxylic acid derivatives, homologs, and salts with formula (I) is generally between 0.01 and 10%, and preferably between 0.5 and 5 wt. %, relative to the total weight of the composition.

Examples of vehicles for application of the compositions include an aqueous or water-alcohol solution, an emulsion of the oil-in-water or water-in-oil type, an emulsified gel, or a two-phase system.

Preferably, the compositions according to the invention are in the form of a lotion, a cream, a milk, a gel, a mask, microspheres or nanospheres, or vesicular dispersions. In the case of vesicular dispersions, the lipids of which the vesicles are made can be of the ionic or nonionic type, or a mixture thereof.

These cosmetic compositions can optionally also contain a moistener, a surfactant, a keratolytic, an anti-inflammatory agent, a complexing agent, an antioxidant, a preservative, a fragrance, or a sunscreen.

These compositions are applied topically in an amount corresponding to the conventional application doses for the type of composition in question (gel, cream, lotion, etc.). For example, in the case of a cream, 0.5 to 3 mg is used, and in particular 1 to 2 mg of cream per $cm^2$ of skin per application, at the rate of one or two applications per day.

The present invention also has as an object novel compounds which are derivatives of 2,5-dihydroxyphenylcarboxylic acid having the following structural formula (III):

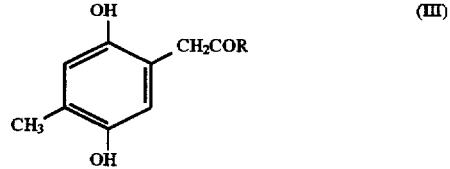

wherein:

R represents the OR' or NHR" radical, R' represents a linear or branched $C_1$-$C_6$ lower alkyl radical, and R" represents a $C_4$-$C_{12}$ alkyl radical.

Examples of compounds with formula (III) include the following:

methyl 2,5-dihydroxy-4-methylphenylacetate,
ethyl 2,5-dihydroxy-4-methylphenylacetate,
propyl 2,5-dihydroxy-4-methylphenylacetate,
isopropyl 2,5-dihydroxy-4-methylphenylacetate,
butyl 2,5-dihydroxy-4-methylphenylacetate,
isoamyl 2,5-dihydroxy-4-methylphenylacetate, and
N-octyl-2-(2,5-dihydroxy-4-methylphenyl)acetamide.

In vitro studies

Certain of the 2,5-dihydroxyphenylcarboxylic acid derivatives, their homologs, and their salts with general formula (I) have been studied by comparison to hydroquinone in equivalent molar quantities in the in vitro tyrosinase activity inhibition test.

According to this test, the quantity of dopachrome formed during the chain of reactions by which tyrosine is converted into melanins is monitored by visible spectrometry at 475 nm. These reactions are catalyzed in vitro by fungal tyrosinase in the presence of a reducing cosubstrate (for example L-dopa in a small quantity) to initiate the hydroxylation reaction of L-tyrosine into L-dopa. The L-dopa is then oxidized catalytically into dopaquinone and then into dopachrome, an intermediate formed prior to the nonenzymatic oxidation reactions that lead to formation of melanins.

Hence, the concentration of dopachrome formed over time both in the presence and in the absence of the inhibitor is measured.

The inhibitor concentrations are established at 50 mol. % relative to the tyrosine concentration in the reaction medium.

The effect of inhibition is expressed by the decrease in the maximum quantity of dopachrome formed (optical density value at 475 nm read from the plateau of the curve) relative to the quantity obtained in the absence of inhibitor.

| Experimental Conditions | |
| --- | --- |
| Reagents: | |
| A - | 0.1M phosphate buffer, pH = 6.5 (Tween 20, 1%) |
| B - | Stock solution of L-tyrosine, 2 × 10$^{-3}$M in A |
| C - | Stock solution of L-dopa, 10$^{-4}$M in A |
| D - | Stock solution of fungal tyrosinase, 2400 units/ml, in A |
| E - | Stock solution of inhibitor, 10$^{-2}$M in A |
| (solutions C and D must be prepared on the day of the experiment). | |
| Results | |
| — | reference cell: 3 ml of A |
| — | test cell: 1 ml of B |
| | 0.1 ml of C |
| | 1.85 ml of A + E |
| — | homogenize and equilibrate at 25° C. |
| — | add 0.05 ml of D |
| — | mix rapidly and observe kinetics by measuring absorbance at 475 nm as a function of time. |

TABLE I

| Compounds | % Inhibition |
| --- | --- |
| OH / CH$_3$ / CH$_2$COOCH$_3$ / OH (2,5-dihydroxy-4-methylphenyl methyl acetate) | −87% |
| OH / CH$_3$ / CH$_2$COOH / OH | −66% |
| OH / CH$_3$ / CH$_3$ / CH$_2$COOH / OH | −59% |
| OH / CH$_3$ / CH$_2$—CH$_2$COOH / OH | −64% |
| OH / CH$_2$—CH$_2$COOH / OH | −42% |
| OH / OH (hydroquinone) | −33% |

As illustrated in Table 1, the 2,5-dihydroxyphenylcarboxylic acid derivatives, their homologs, and their salts of the compositions according to the present invention have melanogenesis-inhibiting activity distinctly superior to that of hydroquinone.

PREPARATION EXAMPLES

Example I

Preparation of methyl 2,5-dihydroxy-4-methylphenylacetate

A mixture of 145.6 g of 2,5-dihydroxy-4-methylphenylacetic acid and 45 g of dry sulfonic acid resin (IRN-77$^R$) is heated under reflux in 4.38 liters of absolute methanol. The mixture is filtered and the filtrate evaporated. The white solid is recrystallized from a mixture of ethyl acetate and heptane (50:50), yielding white crystals with the following characteristics:

Melting point=138.5° C.

Elementary analysis:
Calculated: C% 61.22 H% 6.16 0% 32.62
Actual: 61.23 6.14 32.40

Examples 2 to 6

Using the method described above for Example 1 but replacing the ethanol by the corresponding alcohol, the following compounds were prepared:

Example 2

Ethyl 2,5-dihydroxy-4-methylphenylacetate
White crystals, m.p.=134° C. (isopropyl acetate)
Elementary analysis: $C_{11}H_{14}O_4$
Calculated: C% 62.85 H% 6.71 0% 30.44
Actual: 62.79 6.72 30.32

Example 3

Propyl 2,5-dihydroxy-4-methylphenylacetate
White crystals, m.p.=101° C. (isopropyl ether)
Elementary analysis: $C_{12}H_{16}O_4$
Calculated: C% 64.27 H% 7.19 0% 28.54
Actual: 64.32 7.22 28.45

Example 4

Isopropyl 2,5-dihydroxy-4-methylphenylacetate
White crystals, m.p.=123° C. (water)
Elementary analysis: $C_{12}H_{16}O_4$
Calculated: C% 64.27 H% 7.19 0% 28.54
Actual: 64.13 7.28 28.34

Example 5

Butyl 2,5-dihydroxy-4-methylphenylacetate
White crystals, m.p.=113° C. (water)
Elementary analysis: $C_{13}H_{18}O_4$
Calculated: C% 65.53 H% 7.61 0% 26.86
Actual: 65.58 7.60 27.02

Example 6

Isoamyl 2,5-dihydroxy-4-methylphenylacetate
White crystals, m.p.=99° C. (isopropyl acetate)
Elementary analysis for $C_{14}H_{20}O_4$
Calculated: C% 66.65 H% 7.99 0% 25.36
Actual: 66.47 7.91 25.09

Example 7

Preparation of N-octyl-(2,5-dihydroxy-4-methylphenyl)-acetamide

A solution of 7.75 g of n-octylamine dissolved in 15 ml of dimethylformamide is placed in a solution of 10 g of 5-hydroxy-6-methyl-3H-benzofuran-2-one dissolved in 15 ml of dimethylformamide. After 15 minutes at 100° C., the mixture is evaporated to dryness at reduced pressure. It is treated with 100 ml of ethyl acetate, rinsed with water, dried, then evaporated, yielding a white solid which is recrystallized from isopropyl acetate.

Melting point: 118° C. white crystals
Elementary analysis: $C_{17}H_{27}NO_3$
Calculated: C% 69.59 H% 9.28 N% 4.77 0% 16.36
Actual: 69.50 9.15 4.58 16.66

Example 8

Preparation of 6-(2,5-dihydroxy-4-methoxyphenyl)-hexanoic acid a) Preparation of 6-(2,5-dihydroxy-4-methoxyphenyl)-6-oxohexanoic acid Seven grams of 2-methoxyhydroquinone and 13.6 g of the monomethyl ester of adipic acid in 60 ml of dichloroethane are mixed under nitrogen in a three-necked flask. Thirteen milliliters of boron trifluoride etherate is run in at room temperature. After five hours of refluxing, the reaction medium is poured into a mixture of 40 g of sodium acetate trihydrate and 100 ml of water. The product is extracted with 500 ml of ethyl acetate, washed, dried, and concentrated under vacuum. The residue is treated with a mixture of 1.4 ml of concentrated sulfuric acid, 14 ml of water, and 40 ml of acetic acid at 80° C. for three hours, then the solution is poured into 100 ml of ice water. The precipitate is filtered, washed several times with 20 ml of water, and dried. The solid is recrystallized from a mixture of ethyl acetate and isopropyl ether, yielding yellow crystals with the following characteristics:

Melting point: 165° C.
Elementary analysis: $C_{13}H_{16}O_6$
Calculated: C% 58.20 H% 6.01 0% 35.78
Actual: 58.02 6.09 35.73 b) Preparation of 6-2,5-dihydroxy-4-methoxyphenyl)-hexanoic acid

Two grams of mossy zinc, 0.13 g of mercuric chloride, 0.13 ml of concentrated hydrochloric acid, and 4 ml of water are mixed while stirring. After ten minutes the aqueous phase is-decanted, then the amalgam is rinsed with water. To this amalgam are added a solution of 2.5 g of 6-(2,5-dihydroxy-4-methoxyphenyl)-6-oxohexanoic acid in 20 ml of toluene, then a dilute hydrochloric acid solution (6 ml concentrated HCl and 3 ml of water). After eight hours of refluxing, the solution is poured into 300 ml of ice water. The desired compound is extracted with ethyl acetate (3×100 ml) and washed with water, dried, then evaporated under vacuum. The solid is recrystallized from a mixture of ethyl acetate and heptane to give white crystals with the following characteristics:

Melting point: 142° C.
Elementary analysis: $C_{13}H_{18}O_5$
Calculated: C% 61.41 H% 7.14 0% 31.46
Actual: 61.33 7.20 31.50

EXAMPLES OF COMPOSITIONS

Example 1

Water-in-oil emulsion

| | |
|---|---|
| Glycerin | 5 g |
| Propylene glycol | 10 g |
| Methyl 2,5-dihydroxy-4-methylphenylacetate | 0.5 g |
| Cyclomethicone (cyclopentadimethylsiloxane) | 20 g |
| Abil WO9 (mixture of ethoxylated propoxylated poly-cetyldimethylsiloxane, polyglyceryl isostearate with 4 mols of glycerin, and hexyl laurate) | 3 g |
| Fragrance | 0.1 g |
| Preservatives | 0.2 g |
| Water | qs. 100 g |

In this example, the methyl 2,5-dihydroxy-4-methylphenylacetate can advantageously be replaced by 0.8 g of 2,5-dihydroxy-4-methylphenylhexanoic acid.

Example 2

Water-in-oil emulsion

| | |
|---|---|
| Propylene glycol | 11 g |
| Methyl 2,5-dihydroxy-4-methylphenylacetate | 0.5 g |
| Mineral oil (vaseline) | 20.5 g |
| Sorbitan isostearate (fatty acid esters and sorbitol) | 5 g |
| Miglyol Gel B (hectorite modified by dimethylbenzyl-stearylammonium chloride in glyceryl dicaprylate/dicaprate) | 5 g |
| Coco-caprylate/caprate (esters of $C_8$–$C_{10}$ acids and $C_{12}$–$C_{18}$ fatty alcohol) | 1 g |
| Fragrance | 0.1 g |
| Preservatives | 0.2 g |
| Water | qs. 100 g |

In this example, the methyl 2,5-dihydroxy-4-methylphenylacetate can be replaced by 0.8 g of isoamyl 2,5-dihydroxy-4-methylphenylacetate.

Example 3

Oil-in-water emulsion

| | |
|---|---|
| Ceteareth 20 (cetylstearyl alcohol ethoxylated with 20 moles of ethylene oxide) | 1 g |
| Glycol stearate (ethylene glycol palmitostearate) | 3 g |
| Coco-caprylate/caprate (esters of $C_8$–$C_{10}$ acids and $C_{12}$–$C_{18}$ fatty alcohol) | 5 g |
| Carbomer 934 (carboxyvinyl polymer) | 0.3 g |
| Triethanolamine | 0.9 g |
| 96% Ethyl alcohol | 20 g |
| Methyl 2,5-dihydroxy-4-methylphenylacetate | 1.5 g |
| Glycerin | 3 g |
| Fragrance | 0.1 g |
| Preservatives | 0.2 g |
| Water | qs. 100 g |

In this example, the methyl 2,5-dihydroxy-4-methylphenylacetate can be replaced by 1 g of isopropyl 2,5-dihydroxy-4-methylphenylacetate.

Example 4

Lotion

| | |
|---|---|
| 96% Ethyl alcohol | 50 g |
| PEG (8-mols) (polyethylene glycol No. 8) | 30 g |
| Ethoxydiglycol | 5 g |
| Glycerin | 5 g |
| Methyl 2,5-dihydroxy-4-methylphenylacetate | 3.6 g |
| Water | qs. 100 g |

In this example, the methyl 2,5-dihydroxy-4-methylphenylacetate can be replaced by 2.5 g of 6-(2,5-dihydroxy-4-methoxyphenyl)hexanoic acid.

While the present invention has been disclosed in connection with preferred embodiments thereof, it should be appreciated that there are other embodiments of the present invention which fall within the spirit and scope of the present invention as defined by the appended claims.

What is claimed is:

1. A cosmetic or dermatological composition with a depigmenting action comprising, in a suitable vehicle for topical application to the skin, 2,5-dihydroxyphenylcarboxylic acid derivatives having the following formula:

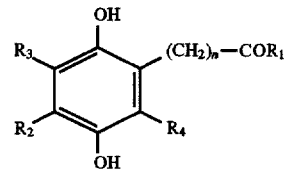

wherein:

$R_1$ represents

r' and r", which are identical or different, represent a hydrogen atom, a $C_1$-$C_{20}$ alkyl radical, a $C_2$-$C_6$ hydroxyalkyl radical, or a $C_3$-$C_6$ polyhydroxyalkyl radical, or r' and r" taken together, with the nitrogen atom, form a heterocycle selected from the group consisting of morpholino, pyrrolidino, piperidino, piperazino and piperazino substituted by a $C_1$-$C_4$ alkyl or a $C_2$-$C_6$ hydroxyalkyl;

the number of carbon atoms in the —$(CH_2)_n$—$COR_1$ chain is less than or equal to 21;

$R_2$ and $R_3$, which are identical or different, represent a hydrogen atom, a linear or branched $C_1$-$C_4$ alkyl radical, or a $C_1$-$C_4$ alkoxy;

$R_4$ represents a hydrogen atom or a linear or branched $C_1$-$C_4$ alkyl radical; and n is an integer of from 0 to 20, provided that, when $R_2$ and $R_3$ represent a hydrogen atom, n is greater than or equal to 2.

2. The composition according to claim 1, wherein the concentration of said 2,5-dihydroxyphenylcarboxylic acid derivatives is between 0.01 to 10 wt. %, relative to the total weight of the composition.

3. The composition according to claim 1, wherein the concentration of said 2,5-dihydroxyphenylcarboxylic acid derivatives is between 0.05 to 5 wt. %, relative to the total weight of the composition.

4. The composition according to claim 1, wherein the suitable vehicle for application to the skin is in the form of at least one member selected from the group consisting of lotions, creams, milk, gels, masks, microspheres, nanospheres, and vesicular dispersions.

5. The composition according to claim 1, wherein the composition further comprises at least one ingredient selected from the group consisting of moisteners, surfactants, keratolytics, anti-inflammatory agents, complexing agents, antioxidants, preservatives, fragrances, and sunscreens.

6. A compound being a derivative of 2,5-dihydroxyphenylcarboxylic acid having the following formula:

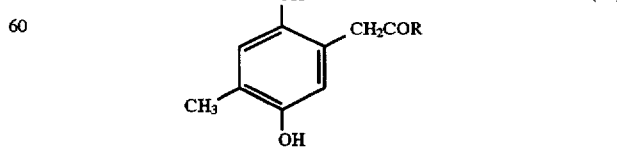

wherein R represents a NHR" radical, and R" represents a $C_4$-$C_{12}$ alkyl radical.

7. The composition according to claim 1, wherein $R_4$ represents a hydrogen atom.

8. The composition according to claim 1, wherein $R_2$ and $R_3$, which are identical or different, represent a hydrogen atom or a linear or branched $C_1$-$C_4$ alkyl radical, provided that when n is 1, at least one of $R_2$ and $R_3$ represent a linear or branched $C_1$-$C_4$ alkyl radical.

9. The composition according to claim 1, wherein said 2,5-dihydroxyphenylcarboxylic acid derivatives are selected from the group consisting of:

3-(2,5-dihydroxy-4'-methylphenyl)-1-N-(ω-carboxydecyl) propylamide,
2,5-dihydroxy-4-methoxyphenylacetamide,
2,5-dihydroxyphenylbutylamide,
2,5-dihydroxyphenylpentylamide, and
2-(2,5-dihydroxy-4-methylphenyl)-N-octylacetamide.

10. The compound according to claim 6, said compound being 2-(2,5-dihydroxy-4-methylphenyl)-N-octylacetamide.

* * * * *

UNITED STATES PATENT AND TRADEMARK OFFICE
CERTIFICATE OF CORRECTION

PATENT NO. : 5,667,792
DATED : September 16, 1997
INVENTOR(S) : Alex JUNINO et al.

It is certified that error appears in the above-indentified patent and that said Letters Patent is hereby corrected as shown below:

Cover Page:    item [62], change "Jul. 17, 1972" to --Jul. 17, 1992--.

Signed and Sealed this

Ninth Day of December, 1997

Attest:

BRUCE LEHMAN

*Attesting Officer*      *Commissioner of Patents and Trademarks*